United States Patent
Fry

(10) Patent No.: US 6,746,461 B2
(45) Date of Patent: Jun. 8, 2004

(54) LOW-PROFILE, SHAPE-MEMORY SURGICAL OCCLUDER

(76) Inventor: William R. Fry, 5690 Broadmoor Bluffs Dr., Colorado Springs, CO (US) 80906

( * ) Notice: Subject to any disclaimer, the term of this patent is extended or adjusted under 35 U.S.C. 154(b) by 0 days.

(21) Appl. No.: 09/930,630

(22) Filed: Aug. 15, 2001

(65) Prior Publication Data

US 2002/0072759 A1 Jun. 13, 2002

Related U.S. Application Data

(60) Provisional application No. 60/225,453, filed on Aug. 15, 2000.

(51) Int. Cl.$^7$ ................................................ A61B 17/08
(52) U.S. Cl. .................... 606/157; 606/158; 606/151
(58) Field of Search .................. 606/151, 153, 606/154, 155, 156, 157, 158, 72, 78; 623/1.19

(56) References Cited

U.S. PATENT DOCUMENTS

| | | | |
|---|---|---|---|
| 3,174,851 A | 3/1965 | Buehler et al. .......... 75/170 |
| 3,351,463 A | 11/1967 | Rozner et al. .......... 75/170 |
| 3,620,212 A | 11/1971 | Fannon, Jr. et al. ...... 128/130 |
| 3,740,839 A | 6/1973 | Otte et al. ............ 29/628 |
| 3,753,700 A | 8/1973 | Harrison et al. ........ 75/175.5 |
| 3,786,806 A | 1/1974 | Johnson et al. ........ 128/92 D |
| 3,890,977 A | 6/1975 | Wilson ................ 128/418 |
| 4,035,007 A | 7/1977 | Harrison et al. ........ 285/381 |
| 4,198,081 A | 4/1980 | Harrison et al. ........ 285/381 |
| 4,205,293 A | 5/1980 | Melton et al. .......... 337/140 |
| 4,485,816 A | 12/1984 | Krumme .............. 128/334 R |
| 4,665,906 A | 5/1987 | Jervis ................ 128/92 YN |
| 4,805,618 A * | 2/1989 | Ueda et al. ............ 128/831 |
| 5,002,563 A | 3/1991 | Pyka et al. ............ 606/222 |
| 5,108,420 A | 4/1992 | Marks ................ 606/213 |
| 5,171,252 A | 12/1992 | Friedland ............. 606/151 |
| 5,282,812 A * | 2/1994 | Suarez, Jr. ............ 606/158 |
| 5,290,289 A * | 3/1994 | Sanders et al. ......... 606/61 |
| 5,562,641 A | 10/1996 | Flomenblit et al. ...... 604/281 |
| 5,601,581 A | 2/1997 | Fogarty et al. ......... 606/159 |
| 5,601,593 A * | 2/1997 | Freitag ............... 623/1.19 |
| 5,733,329 A | 3/1998 | Wallace et al. ........ 623/1 |
| 5,792,155 A | 8/1998 | Van Cleef ............ 606/158 |
| 5,810,853 A | 9/1998 | Yoon .................. 606/151 |
| 5,846,255 A * | 12/1998 | Casey ................ 606/157 |
| 5,853,422 A | 12/1998 | Huebsch et al. ........ 606/213 |
| 5,861,003 A | 1/1999 | Latson et al. .......... 606/213 |
| 5,876,413 A | 3/1999 | Fogarty et al. ......... 606/159 |
| 5,879,366 A | 3/1999 | Shaw et al. ........... 606/213 |
| 5,964,744 A | 10/1999 | Balbierz et al. ........ 604/530 |
| 6,001,110 A | 12/1999 | Adams ............... 606/151 |
| 6,077,291 A | 6/2000 | Das .................. 606/213 |
| 6,090,125 A | 7/2000 | Horton ............... 606/191 |
| 6,096,052 A | 8/2000 | Callister et al. ........ 606/157 |
| 6,099,553 A | 8/2000 | Hart et al. ............ 606/232 |
| 6,113,611 A | 9/2000 | Allen et al. ........... 606/151 |
| 6,117,159 A | 9/2000 | Huebsch et al. ........ 606/213 |
| 6,193,732 B1 | 2/2001 | Frantzen et al. ........ 606/151 |
| 6,258,182 B1 | 7/2001 | Schetky et al. ......... 148/402 |
| 6,269,819 B1 | 8/2001 | Oz et al. .............. 128/898 |
| 6,402,765 B1 * | 6/2002 | Monassevitch et al. .... 606/151 |
| 6,428,548 B1 * | 8/2002 | Durgin et al. ......... 606/142 |
| 6,451,052 B1 * | 9/2002 | Burmeister et al. ...... 623/1.16 |
| 6,517,556 B1 * | 2/2003 | Monassevitch .......... 606/151 |
| 2001/0021858 A1 * | 9/2001 | Bolduc et al. ......... 606/153 |

FOREIGN PATENT DOCUMENTS

| WO | WO 96/01600 | 1/1996 | ........... A61F/2/08 |
|---|---|---|---|
| WO | WO 96/16603 | 6/1996 | ........... A61B/17/04 |

* cited by examiner

*Primary Examiner*—Michael J. Milano
*Assistant Examiner*—Bradford C Pantuck
(74) *Attorney, Agent, or Firm*—Gifford, Krass, Groh, Sprinkle, Anderson & Citkowski, PC

(57) ABSTRACT

A vessel occluding clamp according to the invention provides a pair of opposing jaws connected through a hinge and one or more pieces of shape-memory material associated with the jaws. The shape-memory material exhibits a transition temperature such that when the clamp is exposed to said transition temperature, the jaws of the clamp may close partially or completely to occlude the vessel.

10 Claims, 1 Drawing Sheet

(VESSEL OCCLUDED)

▦ SHAPE MEMORY METAL TO CLAMP

▨ SHAPE MEMORY METAL TO OPEN

▦ PADDING

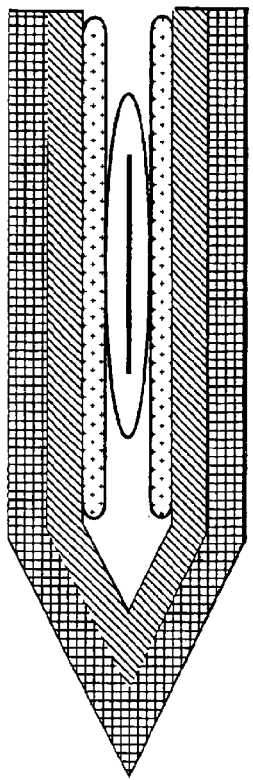
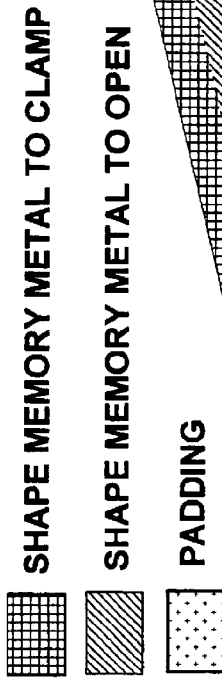
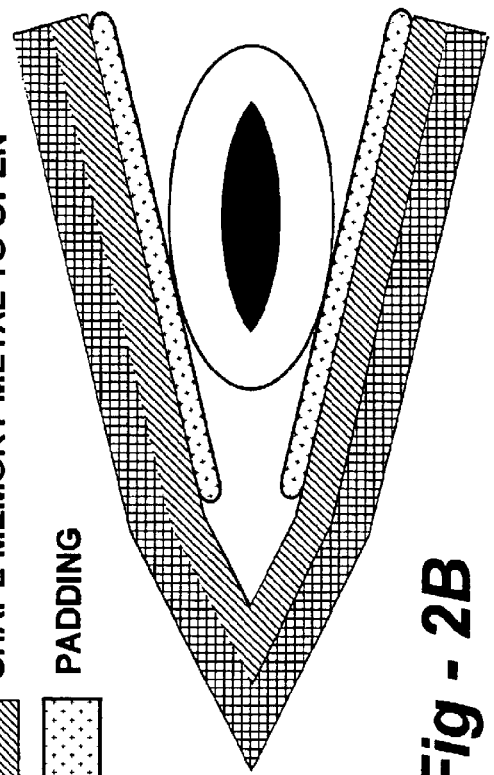
Fig - 2A (VESSEL OCCLUDED)
Fig - 2B (VESSEL PARTIALLY OPEN)
SHAPE MEMORY METAL TO CLAMP
SHAPE MEMORY METAL TO OPEN
PADDING
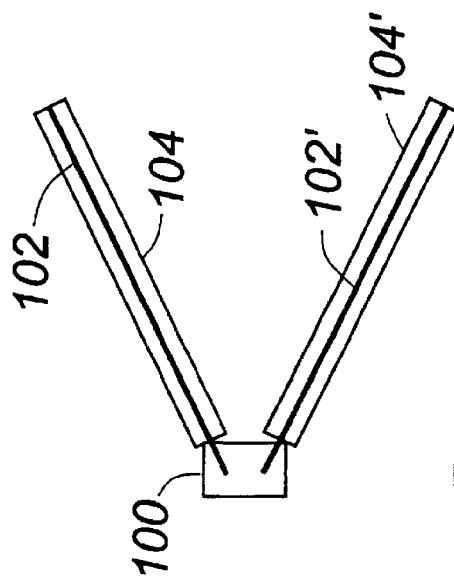
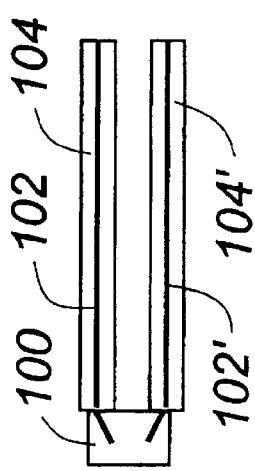
Fig - 1A
Fig - 1B

LOW-PROFILE, SHAPE-MEMORY SURGICAL OCCLUDER

REFERENCE TO RELATED APPLICATION

This application claims priority from U.S. provisional application Serial No. 60/225,453, filed Aug. 15, 2000 now abandoned, the entire contents of which are incorporated herein by reference.

FIELD OF THE INVENTION

This invention relates generally to occlusive medical devices and, in particular, to a clamp which takes advantage of the shape-memory effect to at least temporarily occlude body lumens such as such as blood vessels, bowel, esophagus, stomach, small intestine, colon, and bile ducts.

BACKGROUND OF THE INVENTION

Shape-memory alloys (SMAs) are interesting materials which have the ability to change shape in response to changes in temperature. This ability to "remember" specific shapes corresponds to particular metallurgical phases. If deformed, a SMA can be heated or cooled to invoke a phase transformation which, in turn, induces a change in shape.

Most often, SMAs return to a predetermined shape when heated. When an SMA is cold, or below its transformation temperature, it may be deformed into various shapes and it will retain these shapes. However, when the material is heated above its transformation temperature it undergoes a change in crystal structure which causes it to return to its original shape. If the SMA encounters any resistance during this transformation, it can generate extremely large forces. This phenomenon provides a unique mechanism for remote actuation. For example, shape memory alloys have the ability to act as substitutes for muscle in robotic applications by shortening at a predetermined temperature or electrical current. When cooled, the shape memory metal can then be stretched back out to its initial length.

The most common shape-memory material is an alloy of nickel and titanium called Nitinol. This particular alloy has very good electrical and mechanical properties, long fatigue life, and high corrosion resistance. Above the transition temperature, or transition temperature range, the predominant metallurgical phase of Nitinol is termed austenite. Below the transition, the predominant phase is termed martensite.

The transformation temperatures of SMAs are typically discussed with reference to $M_s$ and $M_f$, the martensitic start and finish temperatures, respectively, and $A_s$ and $A_f$, the austenitic start and finish temperatures, respectively. The transformation between these phases is reversible, such that when alloys are deformed into some first configuration while in the austenitic state, cooled into a martensitic state, deformed into a second configuration, and then re-heated to the austenitic state, the alloy will revert back to the first configuration by virtue of the martensite-to-austenite phase transformation.

Certain SMAs, including Nitinol alloys, also exhibit the ability to form stress-induced martensite as opposed to thermally-induced martensite. In such alloys, the reversible transformation between martensite and austenite occurs by the application and removal of stress rather than heat. These materials are characterized by a temperature $M_d$ which is greater than $A_s$ and represents the maximum temperature at which stress-induced martensite can form. By deforming these alloys at a temperature between $A_s$ and $M_d$, the alloy transforms from its austenitic phase to a stress-induced martensitic phase. Upon release of the stress within this temperature range, the alloy reverts back to its austenitic phase and unstressed configuration. The property of Nitinol which allows it to be deformed in its austenitic state so to cause a transformation to stress-induced martensite that is transformed back to austenite by the release of stress is often termed "pseudoelasticity." Strains of 8% or more are obtained in pseudoelastic Nitinol, thus making this material useful for a wide range of applications where a large amount of recoverable deformation is required.

Over the years, shape memory alloys have been applied to various mechanical devices, including pipe fittings (U.S. Pat. Nos. 4,035,007 and 4,198,081 to Harrison and Jervis), electrical connectors (U.S. Pat. No. 3,740,839 to Otte and Fischer), and switches (U.S. Pat. No. 4,205,293). SMAs have also been used in the medical field. For example, U.S. Pat. No. 3,620,212 to Fannon et al. proposes the use of an SMA intrauterine contraceptive device; U.S. Pat. No. 3,786,806 to Johnson et al. discloses an SMA bone plate, and U.S. Pat. No. 3,890,977 to Wilson proposes the use of an SMA element to bend a catheter or cannula. A useful background is provided in U.S. Pat. No. 4,665,906, which describes medical devices that make use of pseudoelastic Nitinol. In the devices described, austenitic nitinol is deformed to form stress-induced martensite, which is held in its deformed configuration by a restraining member. In this condition, the device is introduced into the body, where it is removed from the restraining member to return to its austenitic state and configuration.

U.S. Pat. No. 4,485,816 discloses the use of a shape memory surgical staple for use in holding the edges of a wound together while it heals. U.S. Pat. No. 5,002,563, discloses the use of shape memory sutures. U.S. Pat. No. 6,001,110 and PCT Publication No. WO 96/16603 describe the use of shape memory materials to address the problem of gastrointestinal bleeding. The '110 patent in particular teaches the use of clips having pseudoelastic properties at body temperature which are used to cause hemostatis of blood vessels located along the gastrointestinal tract. Using pseudoelastic properties found in materials such as Nitinol, the clips are shaped into a first configuration that is useful for ligating blood vessels, deformed to a second configuration to facilitate placement to a desired location within the body, and released from its deformed configuration to allow a spontaneous reversion towards the first configuration.

U.S. Pat. No. 6,193,732 describes a surgical clip made from a metal material which allows the device to be forced into a final shape and then heat treated. Preferably, a shape memory alloy such as Nitinol is used. In that case, the intermediate shape is placed into and held in the desired final condition, and heat treated in that constrained condition at an elevated temperature. After heat treating, the clip is preferably quenched with water or other suitable fluid. According to one embodiment, the clip is manipulated to an open position and locked in place by a secondary member, such as pin. The clip may be opened, for example, by placing the clip in a fixture and forcing the clamp arms open using an angled wedge or other suitable tool. When the clip is constructed of a material having shape memory characteristics, the clamp arms may be completely or partially opened by cooling the surgical clip to a temperature below the transition temperature of the shape-memory alloy. Once opened, the pin is placed between the clamp arms, preferably at or near the apex of the included angle formed by the respective inner clamp surfaces or regions of clamp arms. The pin may be of any convenient cross-sectional shape having an outer dimension sufficient to hold the clamp members in an open condition with a desired operative distal opening.

U.S. Pat. No. 6,096,052 describes a device for occluding a body lumen and, in particular, a contraceptive or sterilization device for occluding a reproductive tract or lumen to prevent the passage of reproductive cells through the tract or lumen. The device generally comprises a tubular member and a mesh member, transversely disposed on the tubular member lumen. The mesh member is permeable to allow for tissue ingrowth, which produces a tissue impregnated mesh occluding the body lumen. The occluding device of the invention can be used in the fallopian tubes of a female patient, the vas deferens of a male patient, or other body lumen. The tubular member is formed from metals such as stainless steel, superelastic or shape memory material such as a nickel-titanium (NiTi) alloy such as Nitinol, platinum, tantalum, gold, or rigid or semirigid biocompatible plastics. In a preferred embodiment, the tubular member is a superelastic material, providing a controlled force on the body lumen during expansion of the tubular member.

Substantially spherical occlusive devices for inserting into body cavities or vesicles are disclosed in U.S. Pat. No. 6,090,125. The devices feature a self-forming shape made from a pre-formed occlusive strand of flexible material. The occlusive strand may be helically coiled or braided and may be adapted with various polymeric fibers. The device is typically introduced through a catheter in the substantially linear inoperable configuration. The invention provides a plurality of such substantially spherical strand portions which nest concentrically with each other in the operable configuration. Preferably, the strand is a wire constructed of a radiopaque material such as a metal or a polymer. Very desirable materials of construction, from a mechanical point of view, are those which maintain their shape despite being subjected to high stress. Particularly preferred are the alloys described in U.S. Pat. Nos. 3,174,851; 3,351,463; and 3,753,700. Especially preferred is the titanium/nickel alloy known as Nitinol.

Despite these applications of shape-memory alloys, certain medical appliances are still in need of improvement. One example is vascular clamps, which are utilized to occlude arteries and veins so that blood flow is stopped during procedures to repair, anastomose, or remove thrombus or foreign objects. Due to the forces needed to close the lumen of an artery, clamps usually have long handles. These handles often get in the way of doing the procedure. As such, any approach that would reduce the profile of such devices or instruments would be welcomed by the medical/surgical community.

SUMMARY OF THE INVENTION

This invention improves upon the existing art by providing a vessel-occluding clamp which takes advantage of the shape-memory effect. Although the invention is particularly suited to cardiovascular applications, the apparatus and methods may be directed to other body lumens besides blood vessels, including bowel, esophagus, stomach, small intestine, colon, and bile ducts. The self-actuating nature of the clamp allows the device work in tight places, be placed through trocars for minimal-access procedures, and forgo the need for conventional or specific applicators.

In the preferred embodiment, a clamp according to the invention a pair of opposing jaws connected through a hinge and one or more pieces of shape-memory material associated with the jaws. For example, the shape-memory material may be in the form of one or more wires which extend from the hinge to each jaw. Although each wire is anchored to a respective jaw, each wire can preferably move within or relative to the jaw to achieve the effect of a strong muscle.

The shape-memory material exhibits a transition temperature such that, when the clamp is exposed to internal body temperatures of the type experienced during a typical surgical procedure, the jaws close to close partially or completely occlude the vessel, and wherein the jaws open below the transition temperature for removal of the clamp or to restore flow through the vessel.

The transition temperature is preferably such that the jaws open in the presence of cooling irrigation. Other stimuli, such as the application of an electrical current, may alternatively be used. In an alternative embodiment, a second shape memory material is used having a second transition temperature which, when reached, causes the jaws to open.

The jaws are substantially parallel to one another and smooth where the vessel is partially or completely occluded so as not to damage the vessel when the jaws are closed. The jaws are also preferably non-locking so that they open only through a change in temperature. As an option, the jaws may include padding where they occlude the vessel, and the padding may be of the type which readily releases from the jaws.

BRIEF DESCRIPTION OF THE DRAWINGS

FIG. 1A is a drawing of a clamp according to the invention in an open condition;

FIG. 1B is a drawing of the clamp of FIG. 1A in a closed condition;

FIG. 2A is a drawing of an alternative embodiment of the invention using multiple shape-memory materials in a closed condition; and FIG. 2B is a drawing of the clamp of FIG. 2A in an open condition.

DETAILED DESCRIPTION OF THE INVENTION

This invention improves upon the existing art by providing a vessel-occluding clamp based upon the shape-memory effect. Although the preferred material is Nitinol, alternative metal alloys and non-metal alternatives may be substituted as technology permits, so long as the desired results described herein are achieved. For example, shape-memory polymers (SMPs) may be used for greater deformation capabilities, high shape stability, enhanced formation techniques, and even biodegradability/absorbability. See "Shape Shifters—Shape-Memory Polymers Find Use in Medicine and Clothing," Scientific American, May, 2001, pp. 20–21, incorporated herein by reference. Thus, in this specification and claims, use of the terms "Nitinol," "shape-memory," and "alloy" should be taken to include any suitable substance(s).

Broadly, this invention disposes of the handle, and leaves the jaws of the clamp attached by a Nitinol hinge. The jaws of the clamp can be made out of plastic, other surgical grade metal, or nitinol. The Nitinol hinge is set to bend at a predetermined angle when subjected to body temperature. This enables the clamp to be easily placed around a vessel in an inactive form (more pliable), after which the patient's body temperature causes the Nitinol to assume its predetermined memory shape and clamp the artery or other vessel.

To remove the clamp, irrigation with cold water or the use of an electrical current can be used. The clamp may optionally use a padded jaw, and may further offer the ability for the padding to break away when pulling the clamp off laterally, as shown in U.S. Pat. No. 5,843,101, the contents of which are incorporated herein by reference.

FIG. 1A is a drawing of a clamp according to the invention in an open condition. FIG. 1B is a drawing of the clamp of FIG. 1A in a closed condition. In this particular embodiment, the shape-memory material takes the form of a wire attached to an anchoring hinge member 100 used as a "muscle." The shape-memory wires 102, 102' may be located within the jaws 104, 104' or, alternatively, on the outside or inside jaw surfaces. A single wire connecting both jaws may also be used.

The shape-memory wire preferably has room to move within or relative to the jaw of the clamp, such that heating causes the wire to pull the jaws of the clamp into the closed condition of FIG. 1B. Manually, the clamp is opened by pulling the jaws of the clamp apart after cooling with cool irrigation or otherwise.

An alternative method of clamping and unclamping utilizes two separate pieces of shape memory metal with different memory shapes (clamped and open) that are bonded together, as shown in FIGS. 2A and 2B. By having the different temperature activation for the two shapes the clamp can be clamped or opened by varying the temperature of the metal. This again could be done with the clamping temperature being higher or lower than the open temperature.

The invention may also take advantage of shape-memory materials which exhibit two memory shapes at two different temperatures. Typically, one of these memory shapes is much more forceful and maintains its shape better than the other. By utilizing this property, the clamp can be made out of a single shape-memory piece that, when heated by body temperature, will clamp the lumen shut. When cooled, it will open enough to allow for clamp removal. This could also be done in reverse with cooling the metal it would clamp and heating make it unclamp.

Body temperature can drop significantly during open operative procedures. In addition, with high-flow carbon-dioxide gas for laparoscopy, local temperatures can drop as well. As such, a clamp according to the invention should be set to clamp at a temperature as low as 33° C. (90° F.). For coronary artery bypass grafting or procedures requiring total circulatory arrest, this temperature may need to be as low as 10° C. Thus, for different procedures, the activating clamping temperature could well be different.

Saline or other irrigants normally used in the course of an operation are either room temperature or warmed. Warmed fluids are usually warmed to 48–50° C. to account for heat loss from pouring the fluids and transferring them to the body. Thus, if unclamping is going to be done by the administration of fluids to heat or cool the clamp, a high temperature should be in the 42–45° C. range and for cooling temperatures of 20–24° C. for those cases where hypothermia is used, then it would be recommended to use higher temperatures for unclamping, which any between 18–45° C. would suffice.

The overall shape of a clamp according to the invention is variable, as long as the following conditions are met:

1) Although the jaws of the clamp may be curved in one way or another, they should clamp in a parallel fashion at the point of occlusion to avoid pinching the vessel or other lumenal structure with excessive force leading to tissue damage or necrosis;

2) When the jaws clamp, they cannot interact with the vessel or bowel wall in such a way as to impail part of the wall; and 3) With or without padding, the surface of the jaws should not interlock in such a way so that they cannot be unlocked, as the clamps according to the invention are intended for temporary occlusion.

In summary, by letting the shape memory material achieve its memory temperature, this invention overcomes not only the forces of the vessel wall, but also the force of the shape memory material to unclamp. Unclamping is activated by either raising the temperature to a higher level to activate it, or cooling the shape memory metal to clamp to a temperature below which it becomes maliable, allowing the clamp to open into an open position to allow for removal or reestablishment of flow. The clamp may be totally or partially occluding, and the amount of opening may vary from as little as 10 to 180 degrees.

I claim:

1. A clamp for at least temporarily occluding a blood vessel or other body lumen, comprising:

a pair of opposing jaws connected through a hinge;

a first shape-memory material associated with the jaws, the first shape-memory material exhibiting a first transition temperature such that, when the clamp is exposed to internal body temperatures during a surgical procedure, the jaws close partially or completely to occlude the vessel; and a second shape-memory material having a second transition temperature which, when reached, causes the jaws to open.

2. The clamp of claim 1, wherein the second transition temperature is such that the jaws open in the presence of cooling irrigation.

3. The clamp of claim 1, wherein the second transition temperature is such that the jaws open through the application of an electrical current and wherein said second transition temperature is higher than said first transition temperature.

4. The clamp of claim 1, wherein the jaws are substantially parallel to one another when the vessel is partially or completely occluded.

5. The clamp of claim 1, wherein the jaws are non-locking so that they open only through a change in temperature.

6. The clamp of claim 1, wherein the jaws are smooth at least where the vessel is occluded.

7. The clamp of claim 1, further including padding on the jaws where they occlude the vessel.

8. The clamp of claim 7, wherein the padding readily releases from the jaws.

9. The clamp of claim 1, wherein the shape-memory materials are in the form of one or more wires which extend from the hinge to each jaw.

10. The clamp of claim 9, wherein each wire is anchored to a respective jaw, but wherein each wire can otherwise move within or relative to the jaw.

* * * * *